United States Patent [19]

Gupta

[11] Patent Number: 4,495,795
[45] Date of Patent: Jan. 29, 1985

[54] PERMEAMETER

[75] Inventor: Krishna M. Gupta, Ithaca, N.Y.

[73] Assignee: Porous Materials, Inc., Ithaca, N.Y.

[21] Appl. No.: 332,955

[22] Filed: Dec. 21, 1981

[51] Int. Cl.³ .............................................. G01N 15/08
[52] U.S. Cl. .................................................... 73/38
[58] Field of Search ............................................ 73/38

[56] References Cited

U.S. PATENT DOCUMENTS

| | | | |
|---|---|---|---|
| 2,345,935 | 4/1944 | Hassler | 73/38 |
| 2,465,948 | 3/1949 | Welge | 73/38 |
| 2,737,804 | 3/1956 | Herzog et al. | 73/38 |
| 2,842,958 | 7/1958 | Sayre, Jr. et al. | 73/38 |
| 3,139,747 | 7/1964 | Ferrell et al. | 73/38 |
| 3,181,346 | 5/1965 | Davies | 73/38 |
| 3,199,341 | 8/1965 | Heuer, Jr. et al. | 73/38 X |
| 3,309,912 | 3/1967 | Boland et al. | 73/38 |
| 3,839,899 | 10/1974 | McMillen | 73/38 |
| 4,253,327 | 3/1981 | Wiley | 73/38 |

Primary Examiner—Gerald Goldberg
Assistant Examiner—Joseph W. Roskos
Attorney, Agent, or Firm—Barnard & Brown

[57] ABSTRACT

An improved sample holder for permeable materials, especially useful in permeameters. The sample holder contains the sample within a pliant sleeve. The sleeve is itself constrained within a constrictor. When pressed into a seat, the constrictor reduces in diameter evenly along its length, holding the sample in the sleeve tightly without gaps for fluid leakage.

12 Claims, 5 Drawing Figures

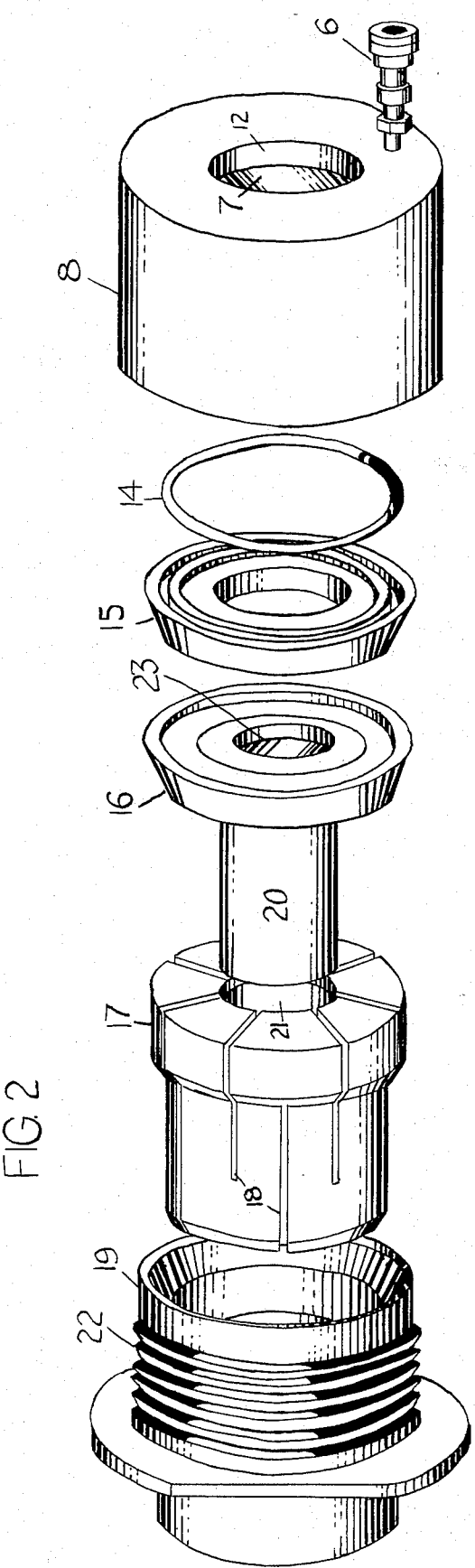

PERMEAMETER

BACKGROUND OF THE INVENTION

The invention pertains to the field of meters for measuring the fluid permeability of solids. More particularly, the invention pertains to apparatus for holding samples for permeability measurement.

The permeameter is an instrument which is well known to the art. A permeameter determines the permeability of a sample by applying a fluid, such as air, under pressure to one side of the sample and measuring the rate at which the fluid flows through the sample. The permeability is then derived as a function of the flow rate, sample size, and pressure differential across the sample.

This method of determining the permeability assumes that the only route for fluid flow is through the sample. Obviously, any fluid flow around the sample instead of through it, or leakage from the system, will adversly effect the accuracy of the results obtained. Thus, the accuracy of the permeameter is dependent upon the method used for holding the sample. Unfortunately, many prior art permeameters were incapable of preventing fluid flow outside of the desired route. A significant portion of the fluid leaked past the sample.

A common method of holding samples used by prior art permeameters is shown in FIG. 4. The sample (30) is compressed between two plates (28) with O-ring seals. The fluid (34) is introduced through the top plate and flows out the bottom, in theory. In practice, however, the fluid is prone to bypassing the sample through its sides, as shown by arrows (30). Also, without careful machining of the top and bottom surfaces of the sample, there can be leakage between the O-rings and the sample.

Other permeameters (FIG. 5) require the sample (30) to be encased in a rigid tube or cylinder (32). Again, the sample must be accurately machined, this time on the curved surface of a cylinder, which is obviously difficult. Gaps (33) are formed between the sample and the cylinder and accuracy is lost. For an example of this system see U.S. Pat. No. 2,686,425, issued to H. W. Dietert in 1954.

Still other permeameters have used a system of encasing the sample in a tapered rubber plug and forcing the plug into a tapered hole. Some examples of this may be found in U.S. Pat. No. 2,521,079 [1950] and U.S. Pat. No. 2,633,015 [1953], both issued to W. L. Morris, as well as in Welge, U.S. Pat. No. 2,465,948 [1948] and Davies, U.S. Pat. No. 3,181,346 [1965]. Although an improvement over the earlier rigid cylinder systems, this method is limited by the ability of the thick rubber plug to conform to irregularities on the sample surface. The plug will compress, to an extent, when forced into the tapered hole, but the compression is limited and uneven, again due to the thickness of the rubber. The thinner end will compress more easily and grip the sample more tightly than the thicker end, which will tend to lead to gaps between the sample and the plug, toward the thicker end. Alternatively, the sample could be overtightened on the thinner end and crushed in an attempt to close the gaps on the thicker end.

Finally, some permeameters have attempted to solve the leakage problem by surrounding the sample in a mercury bath (see TenBrink, 2,724,963 [1955] and Hertzog, U.S. Pat. No. 2,737,804 [1956]. This introduces the use of possibly toxic mercury into the process, and increases the expense and complexity.

It is, therefore, an object of the invention to provide a permeameter which will measure permeability accurately with a minimum of error introduced by leakage around the sample.

It is a further object of the invention to provide a sample holder for permeameter which will accept samples in a variety of sizes, without extensive modification.

It is a still further object of the invention to provide a sample holder for permeameter which will accept samples without extensive machining of the surface, without major error being induced by leakage over an irregular surface.

It is another object of the invention to provide a sample holder for permeameters which meets the above objects and is simple to use and inexpensive to produce, and which does not require the use of liquids or metals surrounding the sample to provide an accurate seal.

Other objects of the invention will become obvious upon reference to the disclosure below.

SUMMARY OF THE INVENTION

A novel improved sample holder for holding samples of permeable material to be tested, as in permeability meters or permeameters, which holds samples to be tested in a thin, pliable, rubber-like sleeve which can conform to surface irregularities of the sample, and which will adapt to a range of sample sizes. The sleeve is evenly compressed by a rigid cylindrical constrictor having alternating longitudinal slots running from its ends along substantially its entire length, enabling the constrictor to reduce in circumference while keeping its sides parallel. The cylinder is constricted by being pressed into a specially shaped seat by a retaining ring.

Thus, the sample is closely held by a sleeve which conforms to its shape without leaving gaps through which fluid can pass. Unlike systems using tapered rubber plugs, the sleeve is pliant and of constant thickness throughout, and is held evenly along its entire length by the cylindrical constrictor. This allows small size differences between samples, as well as surface irregularities, to be easily accommated. Larger differences may be simply, easily and inexpensively accommodated by provision of alternate sleeves and constrictors, allowing use of the permeameter with a wide range of sample diameters.

BRIEF DESCRIPTION OF THE DRAWINGS

FIG. 2 shows an exploded view of the sample holder, as used in the preferred embodiment of the invention.

DESCRIPTION OF THE PREFERRED EMBODIMENT

Figure 1:
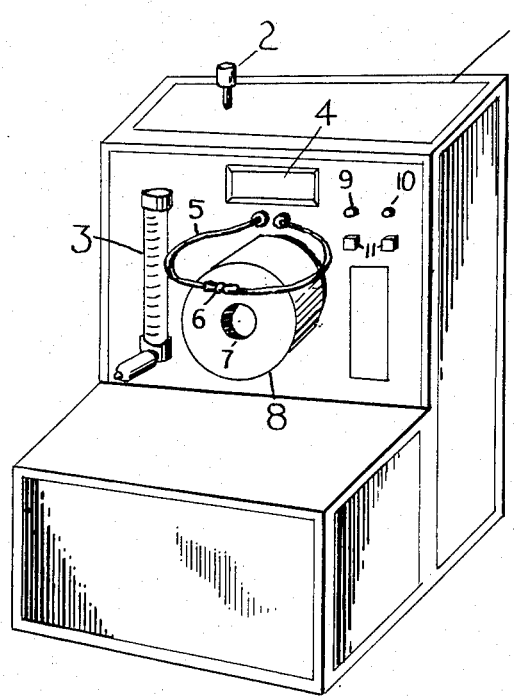
FIG. 1 shows one embodiment of the invention.

FIG. 1 shows a permeameter built according to the teachings of the preferred embodiment of the invention. The permeameter (1) has an inlet (2) for pressurized fluid, such as air. The fluid is led through tubes (5) into a quick-disconnect type fitting on the sample holder retaining ring (8). A window (7) permits the operator to view the sample. To test a sample, it is placed in the sample holder, as described below, and a source of fluid is connected to the inlet (2). The permeameter is turned on by a power switch (9). After calibration, the fluid flow is started by another switch (10). Fluid flow and pressure are read from a flowmeter (3) and differential pressure gauge (4). An indicator light (11) warns of overpressure. The values derived are then processed through a well-known equation along with figures for the sample length and circumference to determine the permeability of the sample.

Turning to FIG. 2, the preferred embodiment of the invention uses a sample holder assembled as shown. The basic parts are the sleeve (20), constrictor (17), retaining ring (8), and seat (19).

The sleeve (20) is made of a molded, non-porous, pliant, rubber-like material. One embodiment of the invention has been successful using Devcon® Flexane®, manufactured by Devcon Corporation, as a sleeve material. It should be recognized, however, that other materials can be substituted without departing from the teachings of the invention. The sleeve material is molded thin enough to conform easily to any irregularity in the cylindrical surface of the sample (19), which is inserted inside the body of the sleeve. A flange (16) is molded on one end of the sleeve to insure a fluid-tight fit with the fluid injection through the retaining ring. The constrictor (17) is made of a rigid material, preferably a plastic such as Teflon® or Delrin®. The constrictor (17) has a cylindrical body made hollow by an inside bore (21) having a constant diameter from end to end. The inside bore (21) of the constrictor is formed such that the uncompressed inside diameter is only slightly larger than the outside diameter of the sleeve (20). The sleeve diameter is, of course, determined by the sample size. The permeameter can thus be adapted to test any size of sample, within the size of the sample holder seat, by changing the size of constrictor and sleeve used.

The cylindrical body of the constrictor, as shown, has an outside diameter which tapers from a greater diameter at the outside end, nearest the retaining ring when inserted into the seat, to a smaller diameter at the inside end, away from the retaining ring (8) and nearest the fluid outlet when inserted into the seat. The change in diameter occurs in four discrete steps. The first step numbered from the outside end of the constrictor, is of constant diameter and the second is a straight sided wedge-shaped section of smoothly varying outside diameter and thickness. The third step comprises substantially the entire length of the body, and is of constant diameter. The fourth step, like the second, is a straight sided wedge-shaped section of smothly varying outside diameter.

The constrictor is formed with slots (18) extending alternately from each end along substantially the entire length of the constrictor. This allows the constrictor to reduce its inside diameter evenly in response to outside pressure, allowing for variations in sample size, and pressing the sleeve uniformly against the sample.

Figure 3:
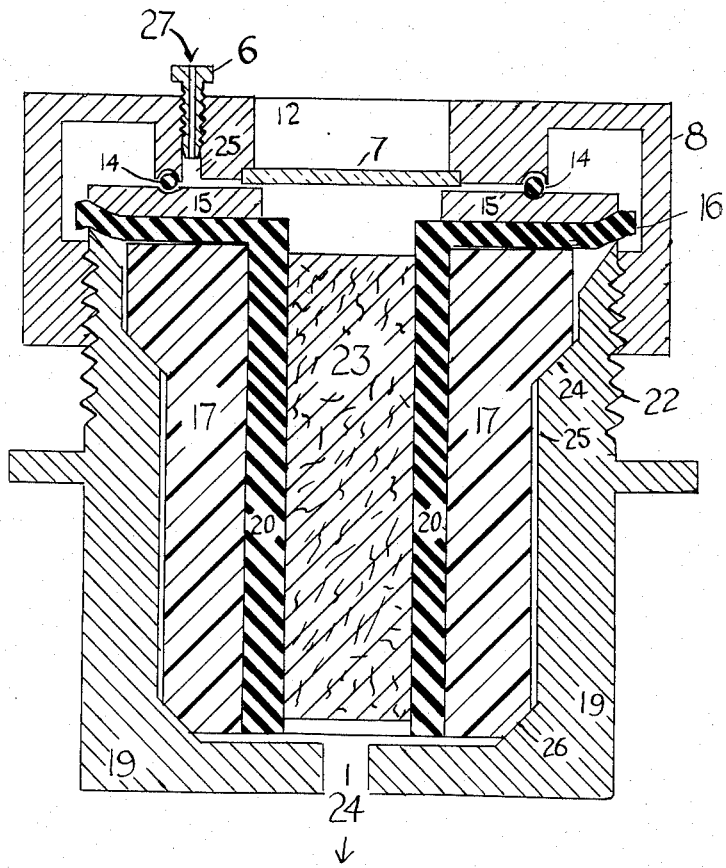
FIG. 3 is a cut-away view of the sample holder of the preferred embodiment of the invention.
Figure 4:
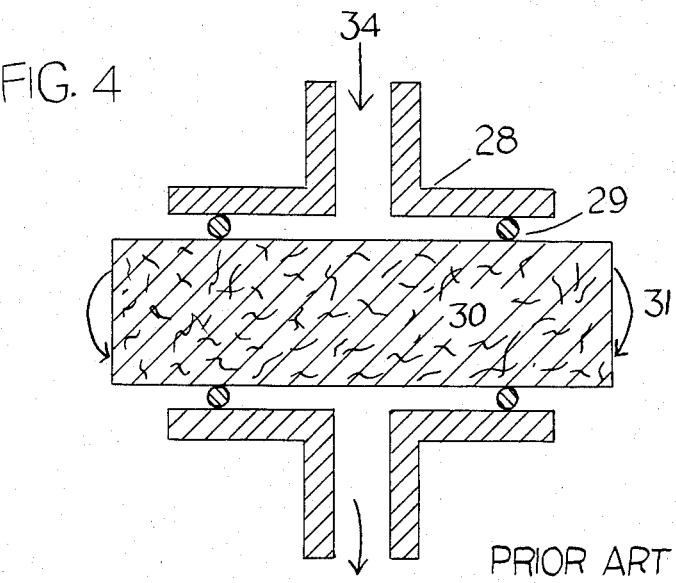
FIGS. 4 and 5 show details of the prior art permeameter sample holders (see above).
Figure 5:
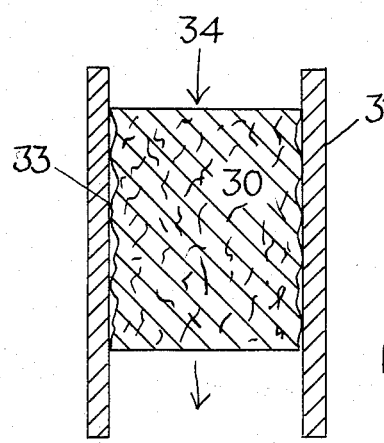

Referring to FIGS. 2 and 3, it will be seen that the sleeve (17) and constrictor (20) slide into a seat (19), which is preferably made of metal, such as brass. The inside seat (19) has a hollow cylindrical body having inside walls of identical shape to the outside of the constrictor, with inside diameter reducing in first through fourth steps of identical length and taper, but slightly larger diameter than those of the constrictor. The retaining ring (8) is tightened by rotation against the threads (22) on the seat. As the constrictor is pressed down into the seat, the tapered second and fourth steps of the constrictor are pressed against the matching second and fourth steps of the seat. This forces the sides of the constrictor inward, closing the slots (18) evenly, top and bottom, causing the constrictor to grip the sleeve (20), and thus the sample (23), tightly and uniformly.

The fluid (27) is introduced under pressure through the fitting (6), preferably of the quick-disconnect type, in the retaining ring (8), and enters the sample (23). Since the sleeve (20) holds the sample (23) evenly, the fluid is constrained to pass only longitudinally through the sample and out through the exit port. Pressure differential is measured between this exit port and the fitting (6) or supply.

In the preferred embodiment, a hole (12) is provided in the retaining ring (8), with a fluid-tight transparent material such as glass forming a window therein (7), so that the operator may observe the sample during testing. This permits the operator to see if the retaining ring has been tightened sufficiently, so that there are no leaks, but not overtightened, crushing the sample.

The preferred embodiment also provides a sample holder cover (15), preferably of a rigid material such as a metal, and an O-ring recessed into the surfaces of the cover and retaining ring. This enhances the quality of the seal between the retaining ring and the flange (16) on the sleeve. This arrangement also permits the retaining ring to rotate more easily during tightening, without abrading the sleeve.

Accordingly, it is to be understood that the embodiments of the invention described herein are merely illustrative of the application of the principles of the invention. Reference herein to details of the illustrated embodiments of the invention are not intended to limit the scope of the claims, which themselves recite those elements regarded as essential to the invention.

I claim:

1. A sample holder for permeable materials, comprising:
   a. pliable, non-porous, sleeve means for closely containing a sample, having smooth, parallel inside and outside walls, whereby the circumference of the sample is entirely enclosed by the sleeve means, leaving the ends exposed;
   b. constriction means of relatively rigid material for compressing the walls of the sleeve means around the sample, surrounding the outside walls of the sleeve means, having an inside diameter which is constant over the length of the constriction means, and is approximately equal to the outside diameter of the sleeve means;
   c. said inside diameter of the constriction means being adapted to reduce to a smaller diameter which is still constant over the length of the constriction means;
   d. seat means for receiving the constriction means, having exit port means for escape of fluid, adapted to acting upon the constriction means whereby as the constriction means is pressed into the seat means, the said constriction means is so constrained as to reduce in inside diameter along its length, evenly compressing the walls of the sleeve means;
   e. retaining ring means for pressing the constriction means into the seat means, having fitting means for introduction of pressurized fluid;
   f. said compression of the walls of the sleeve means causing the inside walls of the sleeve means to seal tightly around the circumference of the sample.

2. The sample holder of claim 1 in which
a. the constriction means comprises: a hollow cylindrical body of rigid material, having sides and first and second flat ends; the body having an inside diameter which is constant from the first to the second end, and an outside diameter which is greater at the first end than at the second; the sides of the body being formed with a plurality of parallel longitudinal slots extending alternately from the first and second ends substantially the entire length of the body; the sides of the body being formed to taper in thickness from a maximum at the first end to a minimum at the second in first, second, third and fourth discrete steps; the first and third steps being of constant diameter and thickness; the third step comprising substantially the entire length of the body; the second and fourth steps being straight sided wedge-shaped sections of smoothly varying outside diameter and thickness; and
b. the seat means comprising: a hollow cylindrical body having inside walls having an inside diameter varying in first, second, third and fourth discrete steps; the second and fourth steps having identical length and taper to the second and fourth steps of the constriction means; the third step having an identical length to the third step of the constriction means; and each of the first, second, third and fourth steps having a slightly larger inside diameter than the outside diameter of the corresponding step of the constriction means; such that when the constriction means is pressed into the seat means by the retaining means the second and fourth steps of the constriction means are pressed inward by the second and fourth steps of the seat means, forcing the longitudinal slots in the sides of the constriction means to reduce in thickness, whereby the diameter of the inside walls of the constriction means is evenly reduced along its length.

3. The sample holder of claim 1 in which the first flat end of the sleeve means further comprises flange means for preventing leakage of fluid between the fitting means of the retaining ring means and the sleeve means.

4. The sample holder of claim 3 further comprising seal means interposed between the retaining ring means and the flange means for permitting differential motion between the said retaining ring means and the said flange means without leakage of fluid.

5. The sample holder of claim 4 in which the seal means comprises a rigid cover plate having groove means for retaining an O-ring, and in which the retaining ring means has a matching groove means for retaining an O-ring, and further comprising an O-ring interposed between the cover plate and the retaining means, whereby the O-ring fits into the groove means on the retaining ring and cover plate.

6. The sample holder of claim 1 in which the retaining ring means further comprises inspection window means for viewing the sample.

7. An improved permeameter of the type having fluidtight sample holder means for holding a sample of material to be tested, said holder having input and output ends on opposite ends of one axis of the sample; pressurized means for supplying a fluid to the input end of the sample holder, whereby the fluid is constrained to pass through the sample and out the outlet end; pressure gauge means for measuring the difference in pressure between the input and output ends of the sample holder; and flowmeter means for measuring the rate of fluid flow through the sample holder means, whereby the permeability of the sample may be determined with reference to fluid flow and pressure differential, in which the improvement comprises an improved sample holder means, comprising:
a. pliable, non-porous, sleeve means for closely containing a sample, having smooth, parallel inside and outside walls, whereby the circumference of the sample is entirely enclosed by the sleeve means, leaving the ends exposed;
b. constriction means of relatively rigid material for compressing the walls of the sleeve means around the sample, surrounding the outside walls of the sleeve means, having an inside diameter which is constant over the length of the constriction means, and is approximately equal to the outside diameter of the sleeve means;
c. said inside diameter of the constriction means being adapted to reduce to a smaller diameter which is still constant over the length of the constriction means;
d. seat means for receiving the constriction means, having exit port means for escape of fluid, adapted to acting upon the constriction means whereby as the constriction means is pressed into to seat means, the said constriction means is so constrained as to reduce in inside diameter along its length, evenly compressing the walls of the sleeve means;
e. retaining ring means for pressing the constriction means into the seat means, having fitting means for introduction of pressurized fluid;
f. said compression of the walls of the sleeve means causing the inside walls of the sleeve means to seal tightly around the circumference of the sample.

8. The improved permeameter of claim 7 in which
a. the constriction means comprises: a hollow cylindrical body of rigid material, having sides and first and second flat ends; the body having an inside diameter which is constant from the first to the second end, and an outside diameter which is greater at the first end than at the second; the sides of the body being formed with a plurality of parallel longitudinal slots extending alternately from the first and second ends substantially the entire length of the body; the sides of the body being formed to taper in thickness from a maximum at the first end to a minimum at the second in first, second, third and fourth discrete steps; the first and third steps being of constant diameter and thickness; the third step comprising substantially the entire length of the body; the second and fourth steps being straight sided wedge-shaped sections of smoothly varying outside diameter and thickness; and
b. the seat means comprises: a hollow cylindrical body having inside walls having an inside diameter varying in first, second, third and fourth discrete steps; the second and fourth steps having identical length and taper to the second and fourth steps of the constriction means; the third step having an identical length to the third step of the constriction means; and each of the first, second, third or fourth steps having a slightly larger inside diameter than the outside diameter of the corresponding step of the constriction means; such that when the constriction means is pressed into the seat means by the retaining ring means the second and fourth steps of the constriction means are pressed inward by the second and fourth steps of the seat means, forcing the longitudinal slots in the sides of the constriction means to reduce in thickness, whereby the diameter of the inside walls of the constriction means is evenly reduced along its length.

9. The improved permeameter of claim 7 in which the first flat end of the sleeve means further comprises flange means for preventing leakage of fluid between the fitting means of the retaining ring means and the sleeve means.

10. The improved permeameter of claim 9 further comprising seal means interposed between the retaining ring means and the flange means for permitting differential motion between the said retaining ring means and the said flange means without leakage of fluid.

11. The improved permeameter of claim 10 in which the seal means comprises a rigid cover plate having groove means for retaining an O-ring, and in which the retaining ring means has a matching groove means for retaining an O-ring, and further comprising an O-ring interposed between the cover plate and the retaining ring means, whereby the O-ring fits into the groove means on the retaining ring and cover plate.

12. The improved permeameter of claim 7 in which the retaining ring means further comprises inspection window means for viewing the sample.

* * * * *